US008821398B2

(12) United States Patent
Kawano et al.

(10) Patent No.: US 8,821,398 B2
(45) Date of Patent: Sep. 2, 2014

(54) CAPSULE MEDICAL APPARATUS GUIDANCE SYSTEM

(75) Inventors: Hironao Kawano, Machida (JP); Johannes Reinschke, Nuremberg (DE); Wolfgang Schmidt, Erlangen (DE)

(73) Assignees: Olympus Medical Systems Corp., Tokyo (JP); Siemens Aktiengesellschaft, Munich (DE)

( * ) Notice: Subject to any disclaimer, the term of this patent is extended or adjusted under 35 U.S.C. 154(b) by 616 days.

(21) Appl. No.: 13/052,509

(22) Filed: Mar. 21, 2011

(65) Prior Publication Data

US 2011/0282165 A1 Nov. 17, 2011

Related U.S. Application Data

(63) Continuation of application No. PCT/JP2009/069961, filed on Nov. 26, 2009.

(30) Foreign Application Priority Data

Nov. 28, 2008 (JP) ................................. 2008-305619

(51) Int. Cl.
*A61B 5/07* (2006.01)
*A61B 1/04* (2006.01)
*A61B 1/00* (2006.01)
*A61B 19/00* (2006.01)

(52) U.S. Cl.
CPC ......... *A61B 1/041* (2013.01); *A61B 2019/2261* (2013.01); *A61B 1/00158* (2013.01)
USPC ........... 600/302; 600/109; 600/117; 600/118; 600/160; 600/178

(58) Field of Classification Search
USPC .................. 600/109, 117–118, 160, 178, 302
See application file for complete search history.

(56) References Cited

U.S. PATENT DOCUMENTS

2004/0141127 A1\* 7/2004 Tsai et al. ..................... 349/137
2006/0169293 A1\* 8/2006 Yokoi et al. ................... 128/899
(Continued)

FOREIGN PATENT DOCUMENTS

JP 2004-229922 8/2004
JP 2007-195961 8/2007
(Continued)

OTHER PUBLICATIONS

International Search Report dated Feb. 23, 2010.

*Primary Examiner* — Jacqueline Cheng
*Assistant Examiner* — Puya Agahi
(74) *Attorney, Agent, or Firm* — Scully, Scott, Murphy & Presser, P.C.

(57) ABSTRACT

A system includes a capsule body having a casing introduced into a subject to perform, in liquid, examination of or treatment on the interior of the subject, the casing containing a permanent magnet, a mass of the casing excluding the magnet being set to be less than a product of a volume of the casing and a density of the liquid; a magnetic field generator that generates a magnetic attraction for the magnet to guide the capsule body; and a magnetic field generation device that controls the magnetic field generator to generate the magnetic attraction by setting a maximum value of the generated magnetic attraction vertically upward to the capsule body, to be equal to a maximum value of the generated magnetic attraction vertically downward to the capsule body, and by setting the maximum values to be less than a value obtained by multiplying a mass of the magnet by a gravitational acceleration.

1 Claim, 9 Drawing Sheets

(56) References Cited

U.S. PATENT DOCUMENTS

| | | | |
|---|---|---|---|
| 2007/0021654 A1* | 1/2007 | Preidel et al. | 600/160 |
| 2007/0142708 A1* | 6/2007 | Yokoi et al. | 600/118 |
| 2007/0142710 A1* | 6/2007 | Yokoi et al. | 600/173 |
| 2007/0221233 A1* | 9/2007 | Kawano et al. | 128/899 |
| 2007/0255099 A1* | 11/2007 | Yokoi et al. | 600/109 |
| 2008/0294006 A1* | 11/2008 | Uchiyama et al. | 600/118 |
| 2009/0171146 A1* | 7/2009 | Fujita | 600/102 |
| 2010/0268026 A1* | 10/2010 | Takizawa | 600/109 |
| 2010/0312077 A1* | 12/2010 | Takahashi et al. | 600/302 |
| 2011/0046443 A1* | 2/2011 | Kawano et al. | 600/118 |

FOREIGN PATENT DOCUMENTS

| | | |
|---|---|---|
| WO | 2007/074888 A1 | 7/2007 |
| WO | 2007/077922 A1 | 7/2007 |

* cited by examiner

SIZE OF MAGNETIC FIELD GENERATION DEVICE (SM)

σ (DENSITY VARIATION WIDTH)

KG

L12

$V_{optmag}$
$(V_{cap} \times \rho_{liq} = M_{cap})$

V2 OPTIMUM SIZE

SIZE OF PERMANENT MAGNET ($V_{mag}$)

$V_{cap} \rho_{liq} G$ — $M_{cap} G$ $F_{dis}$ $|(M_{cap} - V_{cap} \times \rho_{liq}) \times G - F_{dis}|$

CAPSULE MEDICAL APPARATUS GUIDANCE SYSTEM

CROSS-REFERENCE TO RELATED APPLICATIONS

This application is a continuation of PCT international application Ser. No. PCT/JP2009/069961 filed on Nov. 26, 2009, which claims priority from Japanese Patent Application No. 2008-305619 filed on Nov. 28, 2008, the entire contents of each of which are incorporated herein by reference.

BACKGROUND OF THE INVENTION

1. Field of the Invention

The present invention relates to a capsule medical apparatus guidance system that magnetically guides a capsule medical apparatus that is inserted into a subject.

2. Description of the Related Art

In recent years, in the field of endoscopy, capsule body-insertable apparatuses (for example, capsule endoscopes) have been proposed that are provided with an imaging function and a radio communication function and body-insertable apparatus systems have been developed that use capsule endoscopes to acquire in-vivo images of a subject. In order to observe (examine) a subject in vivo, a capsule endoscope is, for example, swallowed by the subject and then, until being naturally excreted, the capsule endoscope moves through the body cavity, such as the internal organs including the stomach and the small intestine, by peristalsis of the internal organs and functions to capture in-vivo images of the subject at intervals of, for example, 0.5 seconds.

While the capsule endoscope moves through the inside of the subject, images that are captured by the capsule endoscope are received by an external image display device via antennae that are arranged on the body surface of the subject. The image display device has a function for communicating by radio with the capsule endoscope and an image memory function and thus sequentially stores the in-vivo images, which are received from the capsule endoscope inside the subject, in the memory. A doctor or a nurse can observe (examine) the inside of the subject and diagnose the subject by using the display of the images stored in the image display device, i.e., in-vivo images of the alimentary canal of the subject.

Proposed is a conventional system that guides a capsule endoscope in a liquid by using a magnetic field, and particularly, a system in which, for guidance of a capsule endoscope in a liquid, the density of the capsule endoscope is equal to or less than the density of the liquid.

SUMMARY OF THE INVENTION

A capsule medical apparatus guidance system according to an aspect of the present invention includes a capsule body that includes a casing which can be introduced into a subject to perform, in a liquid, examination of or treatment on the interior of the subject, the casing containing a permanent magnet, a mass of the casing excluding the permanent magnet being set to be less than a product of a volume of the casing and a density of the liquid; a magnetic field generator that generates a magnetic attraction for the permanent magnet to guide the capsule body; and a magnetic field generation device that controls the magnetic field generator to generate the magnetic attraction by setting a maximum value of magnetic attraction that is generated vertically upward to the capsule body by the magnetic field generation device, to be equal to a maximum value of magnetic attraction that is generated vertically downward to the capsule body by the magnetic field generation device, and by setting the maximum values to be less than a value that is obtained by multiplying a mass of the permanent magnet by a gravitational acceleration.

A capsule medical apparatus guidance system according to another aspect of the present invention includes a capsule body that includes a casing which can be introduced into a subject to perform, in a liquid, examination of or treatment on the interior of the subject, the casing containing a permanent magnet, a mass of the casing excluding the permanent magnet being set to be less than a product of a volume of the casing and a density of the liquid; a magnetic field generator that generates a magnetic attraction for the permanent magnet to guide the capsule body; and a magnetic field generation device that controls the magnetic field generator to generate the magnetic attraction—by setting a maximum value of magnetic attraction that is generated vertically upward for the capsule body by the magnetic field generation device, to be more than a maximum value of magnetic attraction that is generated vertically downward for the capsule body by the magnetic field generation device, and by setting the maximum value to be equal to or more than a value that is obtained by multiplying a mass of the permanent magnet by a gravitational acceleration.

A capsule medical apparatus guidance system according to still another aspect of the present invention includes a first capsule body that includes a first casing which can be introduced into a subject in order to perform, in a liquid, examination of or treatment on the interior of the subject, the first casing containing a first permanent magnet, a mass of the casing excluding the first permanent magnet being set to be less than a product of a volume of the first casing and a density of the liquid; a second capsule body that includes a second casing which can be introduced into the subject in order to perform, in the liquid, examination of or treatment on the interior of the subject, the second casing containing a second permanent magnet, a mass of the second casing excluding the second permanent magnet being set to be less than a product of a volume of the second casing and a density of the liquid; a magnetic field generator that generates a magnetic attraction for the first and second permanent magnets to guide the first and second capsule bodies; a magnetic field generation device that controls the magnetic field generator to generate the magnetic attraction by setting a maximum value of the magnetic attraction that is generated vertically upward to the first and second capsule bodies and a maximum value of the magnetic attraction that is generated vertically downward to the first and second capsule bodies; an input unit for selecting a type of the capsule body that is guided by the magnetic attraction that is generated by the magnetic field generator; and a magnetic field generation control unit that changes the maximum values of the magnetic attraction, which are set in the magnetic field generation device, in accordance with the type of the capsule body that is input by the input unit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Preferred embodiments of a capsule medical apparatus guidance system according to the present invention will be explained in detail below with reference to the drawings. The embodiments do not limit the invention.

First, the relationship between the size of a magnetic field generation device 20 that generates a magnetic attraction for guiding a capsule body 2, which serves as a capsule medical apparatus used for the capsule medical apparatus guidance system, and the size of a permanent magnet 24 in the capsule body 2.

Figure 1:
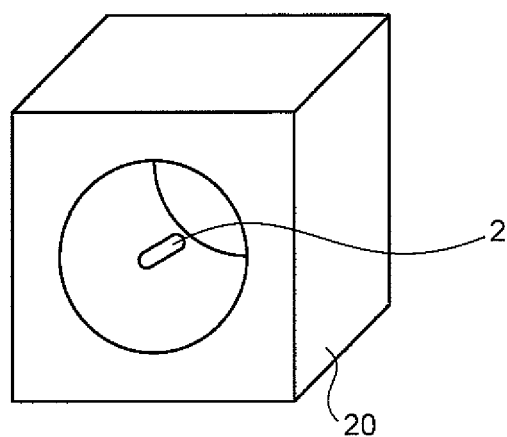
FIG. 1 is a schematic diagram representing the relationship between a capsule body, which is guided, and a magnetic field generation device.

As illustrated in FIG. 1, the magnetic field generation device 20 surrounds the capsule body 2, the magnetic field that is generated by the magnetic field generation device 20 causes a magnetic attraction in the permanent magnet 24 in the capsule body 2, and the magnetic attraction guides the capsule body 2. It is satisfactory if the magnetic field generation device 20 can cause at least a magnetic attraction that is vertical in relation to the capsule body 2.

Figure 2:
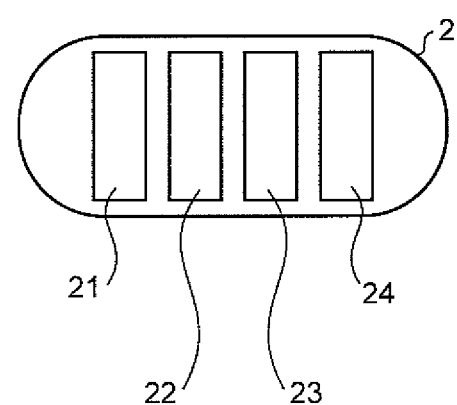
FIG. 2 is a schematic diagram of an overview and configuration of the capsule body.

As illustrated in FIG. 2, the capsule body 2 includes the permanent magnet 24 and further includes an imaging unit 21 that captures external images outside of the capsule body 2, a control circuit 22 that controls the entire capsule body 2, and a power supply 23 that supplies power to the entire capsule body 2. Images that are captured by the imaging unit 21 are transmitted to the outside of the capsule body 2 via a radio unit (not shown). The capsule body 2 is housed in a watertight casing that is almost cylindrical with both ends dome-shaped, i.e., capsule-shaped. The capsule body 2 used herein should have a diameter of approximately 5 to 15 mm and a length of approximately 10 to 40 mm for peroral insertion or a diameter of approximately 5 to 20 mm and a length of approximately 10 to 40 mm for insertion via the anus. The diameter of the esophagus is less than 20 mm, the diameter of the small intestine is approximately 30 mm, and the diameter of the large intestine is approximately 30 to 50 mm. In other words, the diameter of the capsule body 2 for insertion via the anus can be larger than the diameter of the capsule body 2 for peroral insertion, thereby realizing a larger volume for the capsule body 2.

Figure 3:
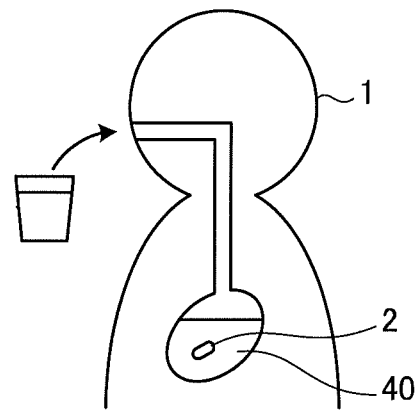
FIG. 3 is a schematic diagram representing the capsule body inserted into a subject.

When observation or examination of the interior of a subject 1 is performed using the capsule body 2, as illustrated in FIG. 3, a liquid 40 is taken beforehand into, for example, the stomach. While the liquid 40 remains in the stomach, the capsule body 2 is perorally inserted into the stomach and the inside of the stomach is observed or examined. During the insertion, the subject 1 lies down in a guidance area in which the capsule body 2 can be guided in the magnetic field generation device 20, the capsule body 2 is then guided in the liquid 40, and an observation in which desired in-vivo images of the subject are captured and an examination in which a tissue is collected are performed.

The liquid that is taken is preferably an optically transparent liquid and preferably consists of mainly water such that image capturing can be performed. If the liquid 40 is water, it is desirable that it be warm with a temperature of approximately 40 degrees Celsius in order not to lower the body temperature of the subject 1, but it may be 30 to 45 degrees Celsius. The density of water in this case is 0.995 g/cm$^3$ at 30 degrees Celsius, is 0.992 g/cm$^3$ at 40 degrees Celsius, and 0.990 g/cm$^3$ at 45 degrees Celsius. The density may be adjusted to approximately 1.0 to 1.1 g/cm$^3$ by mixing a solute, such as sugar, into the water. Increasing the density of the liquid 40 is preferable because the size of the permanent magnet 24 in the capsule body 2 can be increased and accordingly the size of the magnetic field generation device 20 can be further reduced.

When the capsule body is guided vertically in the liquid 40 that is taken into the subject 1, drag occurs while there are the weight and buoyancy of the capsule body. If the drag occurring does not have directionality, the force F necessary for the guidance is represented as follows:

$$F = |M_{cap} - V_{cap} \times \rho_{liq}| \times G + F_{dis} \tag{1}$$

The force F includes the force $F_{down}$ necessary for vertically downward guidance and the force $F_{up}$ necessary for vertically upward guidance. The forces $F_{down}$ and $F_{up}$ are represented as follows (see FIG. 4):

$$F_{down}=|(V_{cap} \times \rho_{liq}-M_{cap}) \times G+F_{dis}| \quad (2)$$

$$F_{up}=|(M_{cap}-V_{cap} \times \rho_{liq}) \times G+F_{dis}| \quad (3)$$

where $M_{cap}$ is the mass of the capsule body 2, $V_{cap}$ is the volume of the capsule body, $\rho_{liq}$ is the density of the liquid 40 in a stomach 1*a*, G is the gravitational acceleration, and $F_{dis}$ is the drag not depending on the direction in which the capsule body 2 is guided.

The causes of occurrence of the drag $F_{dis}$ include the drag of the liquid 40, the density variations of the capsule body 2 due to inconsistencies in designing, motion of the liquid 40 in vivo caused when the body posture changes, motion of the liquid 40 due to the heart rate or breathing, peristalsis of the gastrointestinal canal, and pressure from the walls of the stomach and intestines.

The size SM of the magnetic field generation device 20 necessary for guiding the capsule body 2 is represented as follows:

$$SM=K \times F/M_{mag} \quad (4)$$

where $M_{mag}$ is the mass of the permanent magnet 24 in the capsule body 2. In other words, Equation (4) indicates that the size SM of the magnetic field generation device 20 is relative to the mass $M_{mag}$ of the permanent magnet 24. The size SM of the magnetic field generation device 20 includes a size $SM_{down}$ for vertically downward guidance and a size $SM_{up}$ for vertically upward guidance, which can be represented as follows:

$$SM_{down}=K \times |(V_{cap} \times \rho_{liq}-M_{cap}) \times G+F_{dis}|/M_{mag} \quad (5)$$

$$SM_{up}=K \times |(M_{cap}-V_{cap} \times \rho_{liq}) \times G+F_{dis}|/M_{mag} \quad (6)$$

The relationship between the sizes $SM_{down}$ and $SM_{up}$ and the size $V_{mag}$ of the permanent magnet 24 will be considered. Provided that the density of the permanent magnet 24 is $\rho_{mag}$, the size $V_{mg}$ is represented as follows:

$$V_{mag}=M_{mag}/\rho_{mag}$$

Thus, the size $V_{mag}$ of the permanent magnet 24 can be determined from the mass $M_{mag}$ of the permanent magnet 24. This requires a condition that the capsule body 2 excluding the permanent magnet 24 floats in the liquid 40. In other words, the capsule body 2 satisfies the following equation:

$$V_{cap} \times \rho_{liq} > M_{cap}-M_{mag} \quad (7)$$

Study 1

Figure 4:
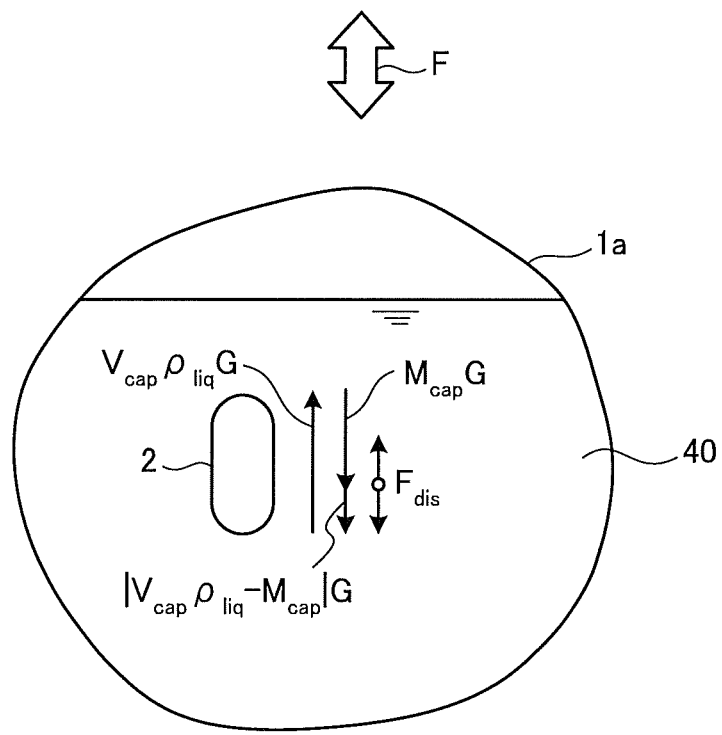
FIG. 4 is a schematic diagram representing drag occurring vertically.
Figure 5:
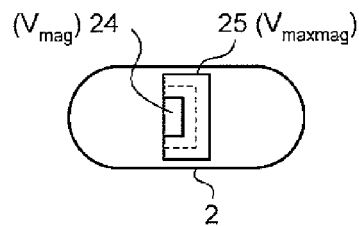
FIG. 5 is a schematic diagram representing the relationship between the maximum size of a permanent magnet that can be arranged in the capsule body and the size of a magnet that is arranged.

First, as illustrated in FIG. 4, a study based on the vertical dynamics of the capsule body 2 in the liquid 40 is conducted, where the mass $M_{mag}$ (the volume $V_{mag}$, hereinafter "size $V_{mag}$") and the sizes $SM_{down}$ and $SM_{up}$ of the magnetic field generation device 20 are variables and the mass of the capsule body 2 excluding the size $V_{mag}$ of the permanent magnet 24 ($M_{cap}+M_{mag}$), the volume $V_{cap}$ of the capsule body 2, and the density $\rho_{liq}$ of the liquid 40 are constants. Note that the size $V_{mag}$ (mass $M_{mag}$) of the permanent magnet 24 can be increased in the capsule body 2 as illustrated in FIG. 5. However, the storage size (mass) of the permanent magnet 24 is a constant and it can be previously secured up to the maximum volume $V_{maxmag}$ (maximum mass $M_{maxmag}$) corresponding to the previous maximum area 25. In this case, the mass of the capsule body 2 excluding the permanent magnet 24 ($M_{cap}-M_{mag}$) is a constant as described above and the constant is set as $M_{cap-mag}$. The sizes can be represented as follows:

$$SM_{down} = K \times |(V_{cap} \times \rho_{liq} - (M_{cap-mag} + M_{mag})) \times G + F_{dis}|/M_{mag} = \quad (8)$$
$$K \times |-G + ((V_{cap} \times \rho_{liq} - M_{cap-mag}) \times G + F_{dis})/M_{mag}|$$

$$SM_{up} = K \times |((M_{cap-mag} + M_{mag}) - V_{cap} \times \rho_{liq}) \times G + F_{dis}|/M_{mag} = \quad (9)$$
$$K \times |G + ((M_{cap-mag} - V_{cap} \times \rho_{liq}) \times G + F_{dis})/M_{mag}|$$

Here, $SM_{down}$ is inversely proportional to $M_{mag}$ and the coefficient of $K/M_{mag}$ satisfies the following equation:

$$(\text{coefficient of } K/M_{mag})=(V_{cap} \times \rho_{liq}-M_{cap-mag}) \times G + F_{dis} > 0 \quad (10)$$

Figure 6:
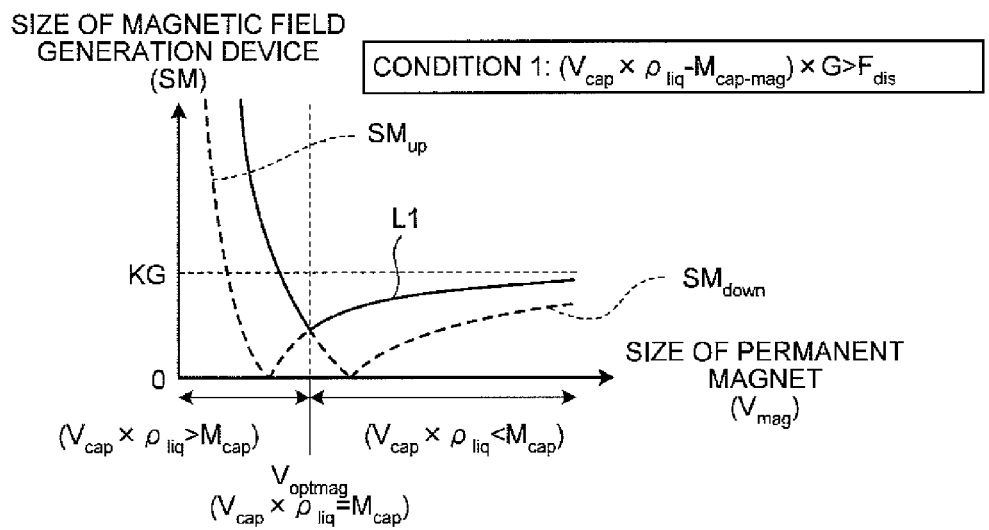
FIG. 6 is a graph representing the relationship between the size of a permanent magnet and the size of the magnetic field generation device under Condition 1.
Figure 7:
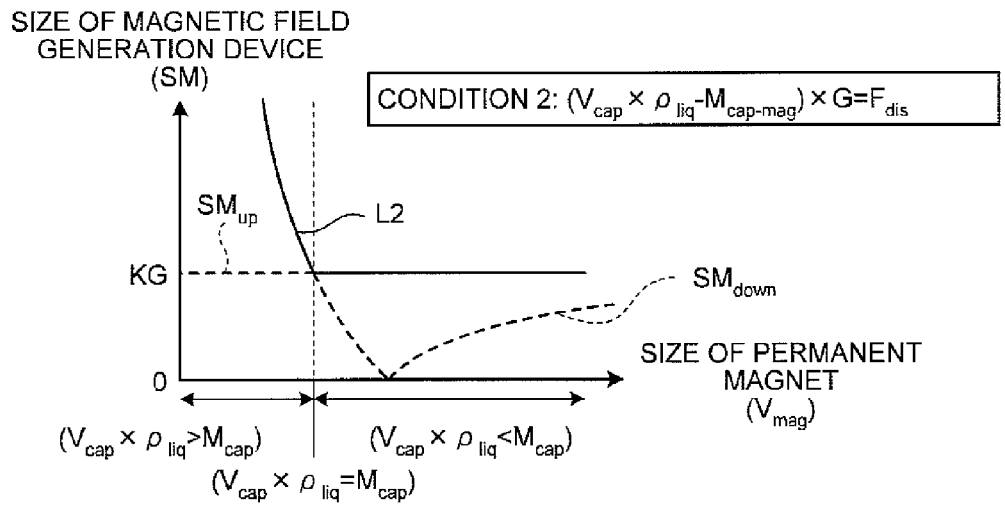
FIG. 7 is a graph representing the relationship between the size of a permanent magnet and the size of the magnetic field generation device under Condition 2.
Figure 8:
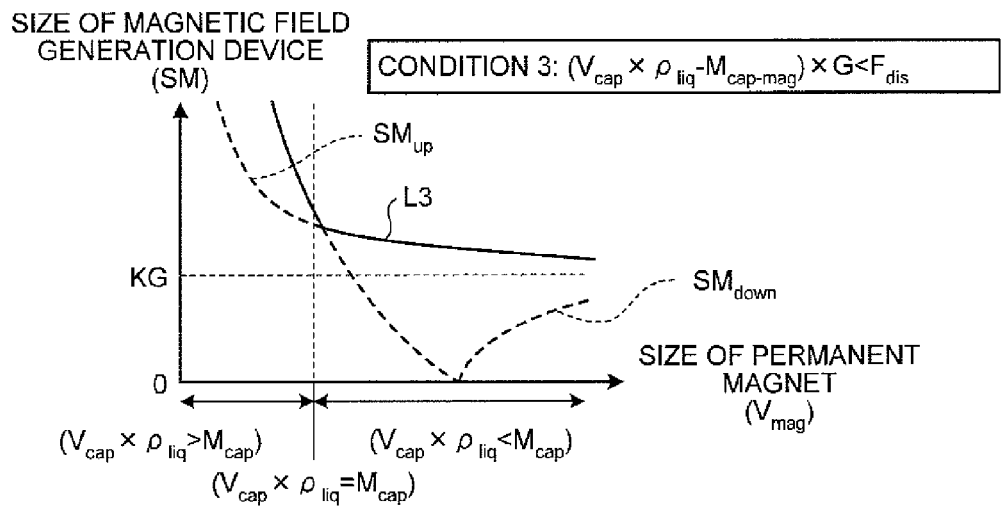
FIG. 8 is a graph representing the relationship between the size of a permanent magnet and the size of the magnetic field generation device under Condition 3.

Thus, as illustrated in FIGS. 6 to 8, the graph of $SM_{down}=f(M_{mag})$ is obtained in a way that the inversely proportional curves in the first and third quadrants are moved in parallel by $-KG$ in the $SM_{down}$ direction and absolute value processing is performed thereon (the area of $SM_{down}<0$ is inverted to the area of $SM_{down}>0$).

In contrast, $SM_{up}$ is inversely proportional to $M_{mag}$ and the positive and negative of the coefficient of $K/M_{mag}$ change according to $F_{dis}$. Thus, the graph of $SM_{up}$ varies depending on the value of $F_{dis}$.

Condition 1 if $(V_{cap} \times \rho_{liq}-M_{cap-mag}) \times G > F_{dis}$, $$(\text{coefficient of } K/M_{mag})=(M_{cap-mag}-V_{cap} \times \rho_{liq}) \times G + F_{dis} < 0 \quad (11)$$

As illustrated in FIG. 6, the graph of $SM_{up}=f(M_{mag})$ is obtained in a way that the inversely proportional curves in the second and fourth quadrants are moved in parallel by $KG$ in the $SM_{up}$ axis direction and absolute value processing is performed thereon (the area $SM_{up}<0$ is inverted to the area of $SM_{up}>0$).

Condition 2 if $(V_{cap} \times \rho_{liq}-M_{cap-mag}) \times G = F_{dis}$, $$(\text{coefficient of } K/M_{mag})=(M_{cap-mag}-V_{cap} \times \rho_{liq}) \times G + F_{dis} = 0 \quad (12)$$

In this case, $SM_{up}=KG$ and the graph thereof is as illustrated in FIG. 7.

Condition 3 if $(V_{cap} \times \rho_{liq}-M_{cap-mag}) \times G < F_{dis}$, $$(\text{coefficient of } K/M_{mag})=(M_{cap-mag}-V_{cap} \times \rho_{liq}) \times G + F_{dis} > 0 \quad (13)$$

As illustrated in FIG. 8, the graph of $SM_{up}=f(M_{mag})$ is obtained in a way that the inversely proportional curves in the first and third quadrants are moved in parallel by $KG$ in the $SM_{up}$ axis direction and the absolute value processing is performed thereon (the area of $SM_{up}<0$ is inverted to the area of $SM_{up}>0$).

As illustrated in FIGS. 6 to 8, when the mass $M_{mag}$ (the size $V_{mag}$) of the permanent magnet 24 is varied, whichever is larger of $SM_{down}$ and $SM_{up}$ is used for the size SM of the magnetic field generation device 20. Note that $(V_{cap} \times \rho_{liq}-M_{cap-mag})$ serving as the boundary condition of the above-described Conditions 1 to 3 represents the difference between the product of the volume of the capsule body 2 and the density of the liquid 40 (the induced buoyancy of the capsule body 2) and the mass of the capsule body 2 excluding the permanent magnet 24.

FIGS. 6 to 8 indicate variations of the size SM of the magnetic field generation device 20 in accordance with the size $V_{mag}$ of the permanent magnet 24 and indicate the results, serving as parameters, under Conditions 1 to 3 as curves L1 to L3. As illustrated in FIGS. 6 to 8, when the size $V_{mag}$ ($M_{mag}$) of the permanent magnet is increased, until the buoyancy of the capsule body 2 becomes equal to the gravitational force of the capsule body 2 ($V_{cap} \times \rho_{liq} = M_{cap}$), the size SM of the magnetic field generation device 20 decreases steeply and monotonically under Conditions 1 to 3. In contrast, when the size $V_{mag}$ ($M_{mag}$) of the permanent magnet 24 further increases, i.e., when $V_{cap} \times \rho_{liq} = M_{cap}$ becomes $V_{cap} \times \rho_{liq} < M_{cap}$, the size SM of the magnetic field generation device 20 increases moderately under Condition 1, does not change under Condition 2, and decreases moderately and monotonically under Condition 3.

In other words, under Condition 1, by setting the size $V_{mag}$ of the permanent magnet 24 to satisfy $V_{cap} \times \rho_{liq} = M_{cap}$ ($=V_{optmag}$), the size SM of the magnetic field generation device 20 can be minimized. Under Condition 2, by setting the size $V_{mag}$ of the permanent magnet 24 to satisfy $V_{cap} \times \rho_{liq} \leq M_{cap}$, the size SM of the magnetic field generation device 20 can be minimized. Under Conditions 1 and 2, it is satisfactory if a setting is made for the magnetic field generation device 20 such that a magnetic attraction corresponding to $F_{dis}$ acts on the capsule body 2. Under Condition 3, by setting the size $V_{mag}$ ($M_{mag}$) of the permanent magnet 24 to satisfy $V_{cap} \times \rho_{liq} < M_{cap}$, the size SM of the magnetic field generation device 20 can be reduced. In this case, it is desirable that the permanent magnet 24 arranged in the capsule body 2 be as large as possible. In other words, because the curve L3 decreases moderately and monotonically under the condition of $V_{cap} \times \rho_{liq} < M_{cap}$, the size SM of the magnetic field generation device 20 can be reduced by increasing $M_{cap}$ to be greater than $V_{cap} \times \rho_{liq}$ within the maximum volume $V_{maxmag}$. In other words, it is satisfactory if the size $V_{mag}$ of the permanent magnet 24 be $V_{maxmag}$.

The size $V_{mag}$ ($M_{mag}$) of the permanent magnet 24 may be set such that the absolute value of $SM_{down}$ in Equation (8) is equal to or less than 0. In this case, because a vertically upward force is generated also for guiding the capsule body 2 vertically downward, it is unnecessary to generate a magnetic attraction vertically downward. Thus, an electromagnet for generating magnetic attraction vertically downward is unnecessary, which further downsizes the magnetic field generation device 20. In this case, the size $V_{mag}$ ($M_{mag}$) of the permanent magnet 24 is set to satisfy the following condition:

(Absolute value of $SM_{down}$)

$$= -G + ((V_{cap} \times \rho_{liq} - M_{cap-mag}) \times G + F_{dis})/M_{mag} \leq 0$$

$$((V_{cap} \times \rho_{liq} - M_{cap-mag}) \times G + F_{dis}) \leq M_{mag} \times G$$

$$F_{dis} \leq (M_{mag} + M_{cap-mag} - V_{cap} \times \rho_{liq}) \times G$$

$$F_{dis} \leq (M_{cap} - V_{cap} \times \rho_{liq}) \times G$$

Accordingly, the force that is generated vertically upward satisfies the following equation:

$$F_{up} = |(M_{cap} - V_{cap} \times \rho_{liq}) \times G + F_{dis}| \leq 2 \times (M_{cap} - V_{cap} \times \rho_{liq}) \times G \quad (14)$$

Thus, it is desirable that the size of the permanent magnet 24 be set such that the force that the magnetic field generation device 20 generates on the capsule body 2 vertically upward be equal to or less than the value obtained by multiplying, by the gravitational acceleration, the value obtained by doubling the difference between the mass of the capsule body 2 and the product of the volume of the capsule body 2 and the density of the liquid 40 (the induced buoyancy of the capsule body 2).

Study 2

Figure 9:
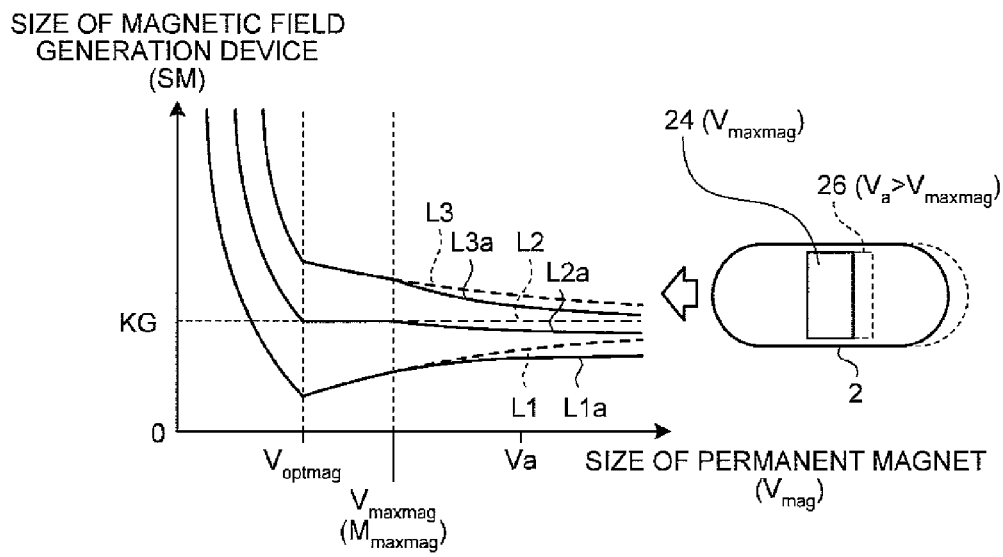
FIG. 9 is a graph representing size variations of the magnetic field generation device in accordance with the size of a permanent magnet in a case where a permanent magnet having a size exceeding the maximum volume of a permanent magnet that can be arranged is arranged and the size of the capsule body is increased.

Regarding arrangement of the permanent magnet 24 with its size $V_{mag}$ exceeding the maximum volume $V_{maxmag}$ of the permanent magnet 24, occupying the area 26 (volume $V_a > V_{maxmag}$), it is preferable that, as illustrated in FIG. 9, the volume $V_{cap}$ of the capsule body 2 be increased in accordance with an increase in the size $V_{mag}$ of the permanent magnet 24. In this case, under any of Conditions 1 to 3, when the maximum volume $V_{maxmag}$ is exceeded, by increasing the volume $V_{cap}$ of the capsule body 2, the size SM of the magnetic field generation device 20 can be reduced from the curves L1, L2, and L3 to the curves L1a, L2a, and L3a. As described above, by increasing the size $V_{cap}$ of the capsule body 2 to increase the size $V_{mag}$ of the permanent magnet 24, the size SM of the magnetic field generation device 20 can be reduced. Particularly for examination of the large intestine using the capsule body 2 via the anus, the capsule body 2 having a large size can be used, and accordingly the magnetic field generation device 20 used in this case can be downsized.

Application Example of Condition 1

The case of Condition 1 means that the drag of the liquid is less than the difference between the buoyancy of the capsule body 2 and the gravitational force of the capsule body 2 excluding the permanent magnet 24. The drag $F_{dis}$ for guiding the capsule body 2 under such a condition is relatively small. For example, the drag $F_{dis}$ is due to the drag of the liquid, the density variations of the capsule body, motion of the liquid caused when the body posture changes, and motion of the liquid due to the heart rate or breathing.

The drag of the liquid can be effectively ignored if a liquid having a low viscosity, such as water, is actually taken. The motion of the liquid due to a change in the body posture or motion of the liquid due to the heart rate or breathing is mainly horizontal motion on the liquid surface, which has less effect vertically. Thus, the drag $F_{dis}$ that affects the guidance is the density variations of the capsule body 2. If the error of the density of the capsule body 2 having a size that is insertable into the body is reduced to be approximately ±3%, the following equation is satisfied:

$$F = F_{dis} = 0.03 \times V_{cap} \times \rho_{liq} \times G$$

If the density of the liquid is approximately 1 g/cm³ (0.9 to 1.1 g/cm³) and the capsule body 2 is for peroral insertion, the following equation is satisfied:

$$F < 0.03 \times (0.75^2 \times 3.14 \times 4.00) \times 1.10 \times 9.81 = 2.3 \text{ (mN)}$$

Because the capsule body 2 can be guided with a very small force F, the magnetic field generation device 20 can be downsized. Furthermore, by reducing the error of the density of the capsule body 2 to be approximately ±1%, the force necessary for the guidance can be reduced to a third, which downsizes the magnetic field generation device 20. In consideration of operational safety, a magnetic field generation device may generate a force of 1.1 to 2 times the force F necessary for guidance.

Guiding the capsule body 2 under Condition 1 with a relatively small drag $F_{dis}$ can be applied to the following examinations:

1) Peroral Insertion and Examination of the Cardiac End and the Stomach and, if Necessary, of the Duodenum, the Small Intestine, and the Large Intestine In this case, first, the capsule body 2 is swallowed in the lateral position and is represented temporarily at the cardiac end to capture images of the cardiac end. The capsule body 2 is then dropped into the stomach. Thereafter, water and a blowing agent are taken to expand the stomach. The blowing agent may be taken before the capsule body 2 is swallowed.

Thereafter, the capsule body 2 is guided in the liquid in the stomach, the posture of the subject is changed, and the entire stomach is observed using the capsule body 2. The capsule body 2 is then guided to the vicinity of the pylorus and is sent to the duodenum by peristalsis of the pylorus. Thereafter, images of the intestinal tracts from the duodenum are captured using peristalsis.

2) Insertion Via Anus and Examination of Large Intestine

In this case, first, a peristalsis inhibitor to inhibit the peristalsis of the large intestine is preferably administered perorally or via the anus. The capsule body 2 and a liquid are then introduced via the anus. The liquid, such as an isotonic solution, may be introduced perorally beforehand. The capsule body 2 is then guided through the large intestine, which is expanded with the liquid, the posture is changed, and the large intestine is observed using the capsule body 2. The capsule body 2 that is inserted into the anus preferably has a size equal to or less than 20 mm×40 mm (length×diameter). In other words, the capsule body 2 preferably has a diameter with which it can pass through the large intestine easily and a length with which it can come back to the anus.

Application Examples Under Conditions 2 and 3

On the other hand, under Conditions 2 and 3, the drag $F_{dis}$ in the liquid is equal to or more than the difference between the buoyancy of the capsule body 2 and the gravitational force of the capsule body 2 excluding the permanent magnet 24. In this case, it is preferable that the size $V_{mag}$ of the permanent magnet 24 of the capsule body 2 be set to satisfy $V_{cap} \times \rho_{liq} < M_{cap}$ and the permanent magnet arranged in the capsule body 2 be as large as possible. Particularly, under Condition 2, the size SM of the magnetic field generation device 20 does not change even if the size $V_{mag}$ of the permanent magnet 24 is increased, but it is preferable that the size $V_{mag}$ of the permanent magnet 24 be large in consideration of a force that acts on a different direction, i.e., the horizontal direction.

The state under Conditions 2 and 3 is a case in which a significantly large drag occurs in vivo and $F_{dis}$ is supposed to be caused by the peristalsis of the gastrointestinal canal or pressure from the walls of the stomach and intestines. For example, the force generated due to the peristalsis of the gastrointestinal canal includes a force necessary for passing through the pylorus. The force necessary for passing through the pylorus requires approximately 100 mN. In this case, Condition 1 cannot be satisfied if the capsule body is insertable into the subject 1.

To make the capsule body 2 satisfy Condition 1, it is required that a permanent magnet with 10 g (=100 mN/(9.8 m/s²)) be arranged in the capsule body 2. In other words, because the density of the liquid 40 is approximately 1, the size $V_{mag}$ of the capsule body 2 needs to be at least equal to or more than 10 cm³. However, for peroral insertion, the maximum size of the capsule body 2 is φ15 mm×40 mm, i.e., the maximum size of the capsule body is approximately 7.0 cm³, and thus Condition 1 cannot be satisfied.

Regarding guidance of the capsule body 2 in the small intestine and the large intestine, even if the speed at which the capsule body 2 is guided is approximately 1 mm/s, the force necessary for the guidance against the pressure from the intestinal wall is equal to or more than 200 mN according to experiments. Thus, this case also cannot satisfy Condition 1. Regarding the peristalsis that occurs in the esophagus, prediction of similar results can be easily obtained.

Examinations that require guidance of the capsule body 2 under Conditions 2 and 3 include the following cases:
1) perorally inserted and guided for observation of the esophagus,
2) perorally inserted and, after observation of the stomach, guided to pass through the pylorus,
3) perorally inserted and guided to observe the small intestine,
4) perorally inserted and guided to observe the large intestine, and
5) inserted via the anus and guided to observe the large intestine.

It is preferable that the liquid 40 be taken perorally when the capsule body 2 is inserted perorally and that the liquid 40 be introduced into the subject 1 via the anus when the capsule body 2 is inserted via the anus. Furthermore, even when the capsule body 2 is inserted perorally, if it is guided through the large intestine, the liquid 40 may be introduced to the subject 1 via the anus. Furthermore, regarding insertion of the capsule body 2 into the subject 1 via the anus, the size $V_{mag}$ of the capsule body 2 can be increased to a maximum of approximately φ20 mm×40 mm. In this case, because the size of the permanent magnet 24 that can be arranged in the capsule body 2 can be also increased, the magnetic field generation device 20 can be downsized.

Study 3

If the magnetic field generator of the magnetic field generation device 20 is arranged only below the subject 1 and thus the magnetic field generation device 20 does not cover the subject, the enclosed feeling of the subject can be eliminated and the examiner can easily approach the subject under examination.

Figure 10:
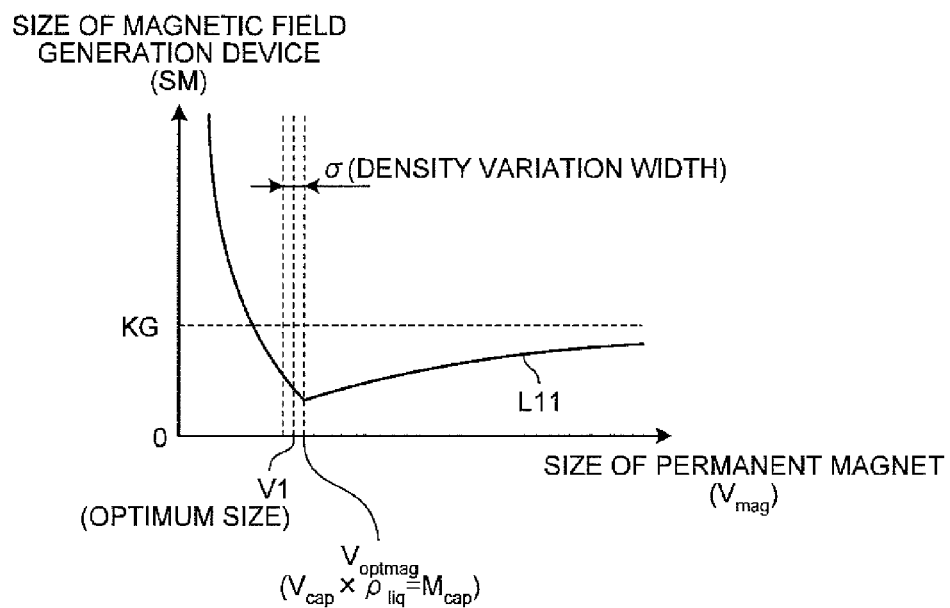
FIG. 10 is a graph that describes how the optimum size of a permanent magnet is determined when the magnetic field generation device is arranged vertically downward with respect to the capsule body and the density of the capsule body is not constant.

However, because such a magnetic field generation device can generate a magnetic attraction only downward, it is necessary to float the capsule body 2 in the liquid 40. In this case, as illustrated in FIG. 10, the density variations of the capsule body 2 occur in the side of the area of $V_{cap} \times \rho_{liq} > M_{cap}$ from the point of $V_{cap} \times \rho_{liq} = M_{cap}$ on the curve L11, i.e., the side of the area in which the size $V_{mag}$ of the permanent magnet 24 is small, and it is satisfactory if the center of the density variation width σ is determined as an optimum size V1 of the permanent magnet 24.

Figure 11:
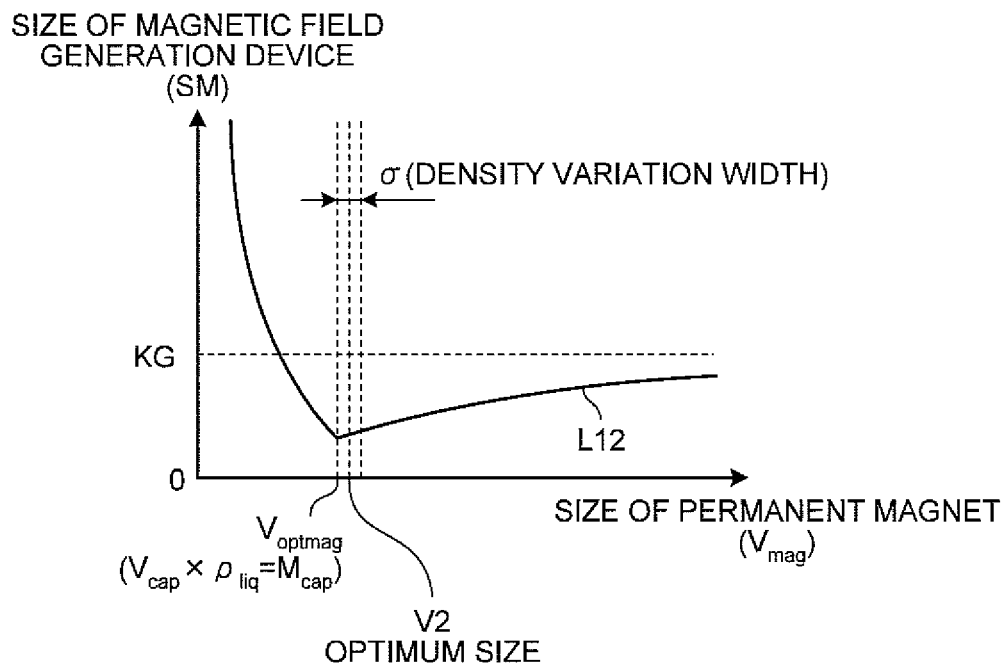
FIG. 11 is a graph that describes how the optimum size of a permanent magnet is determined when the magnetic field generation device is arranged vertically upward with respect to the capsule body and the density of the capsule body is not constant.

In contrast, if the magnetic field generator of the magnetic field generation device is attached to an arm and the magnetic field generator is arranged only above the subject 1, as illustrated in FIG. 11, the density variations occur in the side of the area of $V_{cap} \times \rho_{liq} < M_{cap}$ from the point of $V_{cap} \times \rho_{liq} = M_{cap}$ of the curve L12, i.e., the side of the area in which the size $V_{mag}$ of the permanent magnet 24 is large, and it is satisfactory if the center of the density variation width σ is determined as an optimum size V2 of the permanent magnet 24.

Study 4

Figure 12:
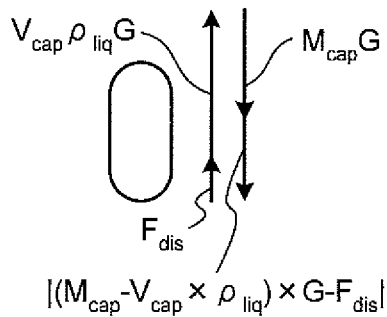
FIG. 12 is a schematic diagram representing drag occurring only vertically upward.

When the capsule body 2 is guided vertically in the liquid 40 that is introduced into the subject 1, drag occurs while the capsule body 2 has weight and buoyancy. Here, a case is considered in which drag occurs only vertically upward. In this case, the force F necessary for the guidance includes, as illustrated in FIG. 12, a force $F_{down}$ necessary for vertically downward guidance and a force $F_{up}$ necessary for vertically upward guidance. The forces $F_{down}$ and $F_{up}$ are represented as follows:

$$F_{down} = |(V_{cap} \times \rho_{liq} - M_{cap}) \times G + F_{dis}| \quad (15)$$

$$F_{up} = |(M_{cap} - V_{cap} \times \rho_{liq}) \times G| \quad (16)$$

Note that the drag that occurs vertically upward includes the surface tension of the liquid surface and the force for passing through the pylorus in the posture with the pylorus in a low position.

In this case, the size SM of the magnetic field generation device 20 necessary for guiding the capsule body 2 includes a size $SM_{down}$ for vertically downward guidance and a size $SM_{up}$ for vertically upward guidance. The sizes $SM_{down}$ and SM up can be represented as follows:

$$SM_{down}=K\times|(V_{cap}\times\rho_{liq}-M_{cap})\times G+F_{dis}|\div M_{mag} \quad (17)$$

$$SM_{up}=K\times|(M_{cap}-V_{cap}\times\rho_{liq})\div M_{mag} \quad (18)$$

Figure 13:
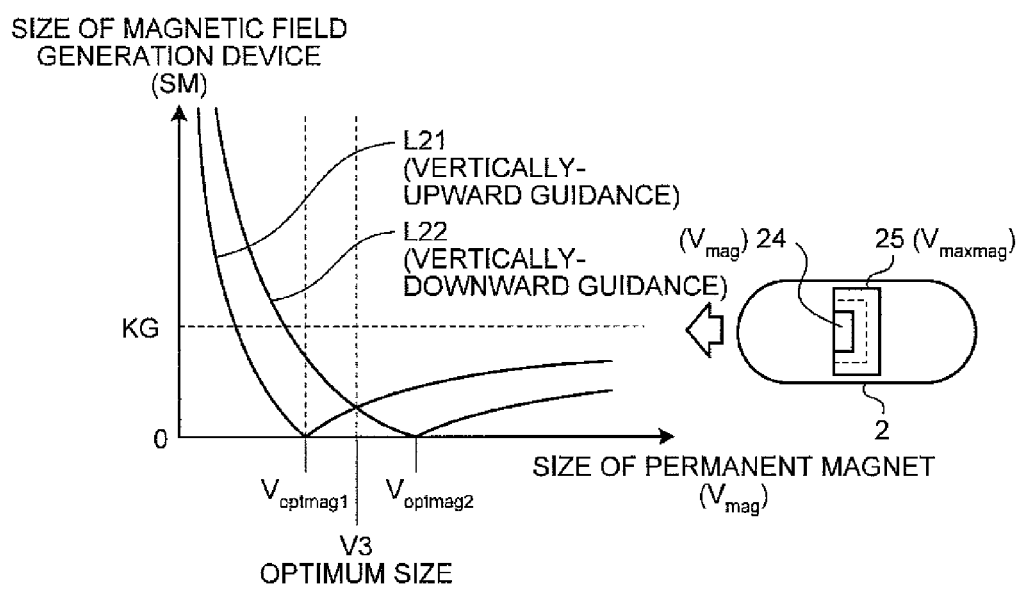
FIG. 13 is a graph and a diagram representing size variations of the magnetic field generation device in accordance with the size of a permanent magnet in a case where drag occurs only vertically upward.

This case also satisfies Equation (7) under the condition that the capsule body 2 excluding the permanent magnet 24 floats in the liquid 40. The relationship of the size SM of the magnetic field generation device 20 with respect to the size $V_{mag}$ (mass $Mm_{ag}$) of the permanent magnet 24 in this case is indicated, as illustrated in FIG. 13, by the curve L21 for vertically upward guidance and the curve L22 for vertically downward guidance that indicate characteristic curves that are different depending on the guidance directionality.

In this case, the condition for minimizing the size SM of the magnetic field generation device 20 can be obtained as the intersection of the curves L21 and L22. In other words, $F_{dis}=2(M_{cap}-V_{cap}\times\rho_{liq})\times G$ can be obtained from the following equation:

$$K\times|(V_{cap}\times\rho_{liq}-M_{cap})\times G+F_{dis}|\div M_{mag}$$
$$=K\times|(M_{cap}-V_{cap}\times\rho_{liq})\times G|\div M_{mag} \quad (19)$$

Thus, the size SM of the magnetic field generation device 20 can be minimized by setting the size $V_{mag}$ of the permanent magnet 24 in the capsule body 2 such that the value obtained by doubling the difference between the gravitational force and the buoyancy of the capsule body 2 is equal to the drag that the magnetic field generation device generates on the capsule body 2 vertically upward. In other words, the minimum value can be obtained with respect to the composite curve of curve portions of the curves L21 and L22, where the size SM of the magnetic field generation device 20 is large. The optimum size of the permanent magnet 24 here is the size V3 indicated in FIG. 13 and is the value at the intersection of the curve L21 and the curve L22. The force that the magnetic field generation device 20 generates on the capsule body 2 vertically upward or downward is the difference between the mass of the capsule body 2 and the product of the volume of the capsule body 2 and the density of the liquid 40 (the buoyancy applied to the capsule body 2).

Application Example Corresponding to Study 4

Guiding the capsule body 2 with a drag that is generated only vertically upward can be applied to the following examinations:

1) Drag is due to the surface tension of the liquid and the cardiac end and the stomach and, if necessary, the duodenum, the small intestine, and the large intestine are examined.

In this case, first, the capsule body 2 is swallowed in the lateral position and is represented temporarily at the cardiac end to capture images of the cardiac end. The capsule body 2 is then dropped into the stomach. Thereafter, water and a blowing agent are taken to expand the stomach. The blowing agent may be taken before the capsule body 2 is swallowed. Thereafter, the capsule body 2 is guided in the liquid in the stomach, the posture of the subject is changed, and the entire stomach is observed using the capsule body 2. The capsule body 2 is then guided to the vicinity of the pylorus and is sent to the duodenum by peristalsis of the pylorus. Thereafter, images of the intestinal tracts from the duodenum are captured using peristalsis.

During observation of the stomach, when the capsule body 2 is guided from the liquid surface into the liquid, a surface tension of 0.7 mN to 3.0 mN of the water (liquid) occurs as a drag. When the capsule body 2 with an exterior formed of resin (Polycarbonate) is sunk such that its longitudinal axis turns downward, the surface tension of the water (liquid) that acts on the capsule body 2 is 0.7 mN if the capsule body 2 has ϕ5 mm, is 1.6 mN if the capsule body 2 has ϕ11 mm, and is 2.3 mN if the capsule body 2 has ϕ15 mm. In other words, the surface tension is in proportion to the diameter of the capsule body 2.

2) Drag is a repulsion caused when passing through the pylorus and the esophagus, the stomach, the duodenum, the small intestine, and the large intestine are examined In this examination, when causing the capsule body 2 to pass through the pylorus, the posture is set in the right lateral recumbent position and a force necessary to pass the capsule body 2 through the pylorus is generated so that the capsule body 2 actively passes through the pylorus. The force necessary for passing through the pylorus is approximately 100 mN. In this case, the capsule body 2 can be inserted into the duodenum accurately in a shorter time compared to the case in which the capsule body 2 is caused to pass through the pylorus by peristalsis. Accordingly, more of the intestinal canals from the duodenum can be observed after observation of the stomach during the life of the battery of the capsule body 2.

Study 5

When the capsule body 2 is guided vertically, if a drag $F_{dis1}$ that is caused with directionality and a drag $F_{dis2}$ working only vertically upward coexist, the size SM of the magnetic field generation device 20 necessary for guiding the capsule body 2 includes a size $SM_{down}$ for vertically downward guidance and a size $SM_{up}$ for vertically upward guidance. The sizes $SM_{down}$ and $SM_{up}$ can be represented as follows:

$$SM_{down}=K\times(|(V_{cap}\times\rho_{liq}-M_{cap})\times G+F_{dis1}+F_{dis2}|)\div M_{mag} \quad (20)$$

$$SM_{up}=K\times|(M_{cap}-V_{cap}\times\rho_{liq})\times G+F_{dis1}|\div M_{mag} \quad (21)$$

This case also satisfies Equation (7) under the condition that the capsule body 2 excluding the permanent magnet 24 floats in the liquid 40.

Regarding the relationship between the size SM of the magnetic field generation device 20 with respect to the size $V_{mag}$ (mass $M_{mag}$) of the permanent magnet 24, $SM_{up}$ can be categorized as in the case of Study 1 under the following Conditions 1 to 3:

$(V_{cap}\times\rho_{liq}-M_{cap-mag})\times G>F_{dis1}$      Condition 1

$(V_{cap}\times\rho_{liq}-M_{cap-mag})\times G=F_{dis1}$      Condition 2

$(V_{cap}\times\rho_{liq}-M_{cap-mag})\times G<F_{dis1}$      Condition 3

Figure 14:
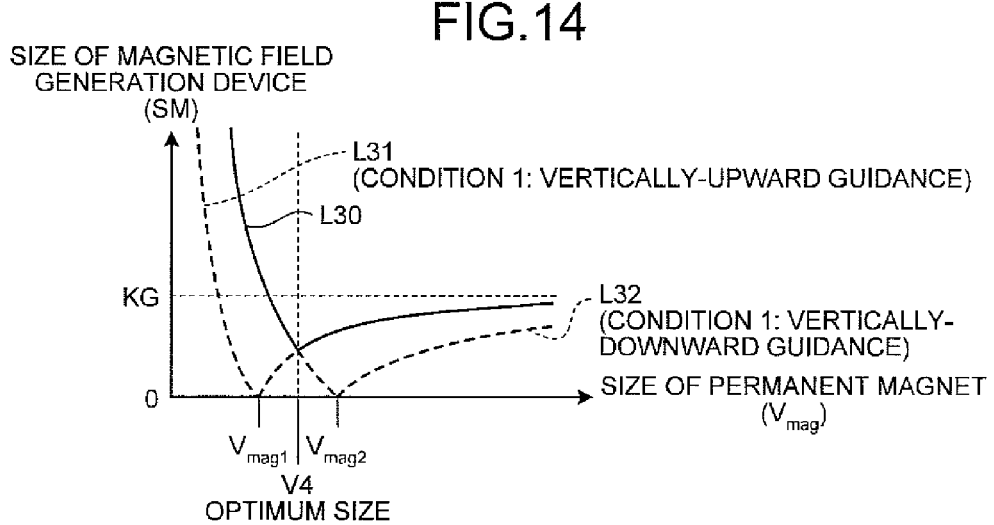
FIG. 14 is a graph representing the relationship between the size of a permanent magnet and the size of the magnetic field generation device under Condition 1 of Study 5.
Figure 15:
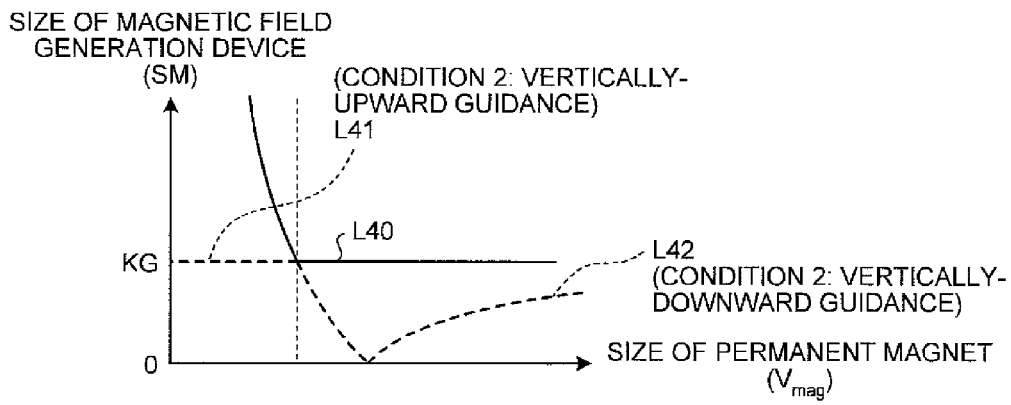
FIG. 15 is a graph representing the relationship between the size of a permanent magnet and the size of the magnetic field generation device under Condition 2 of Study 5.
Figure 16:
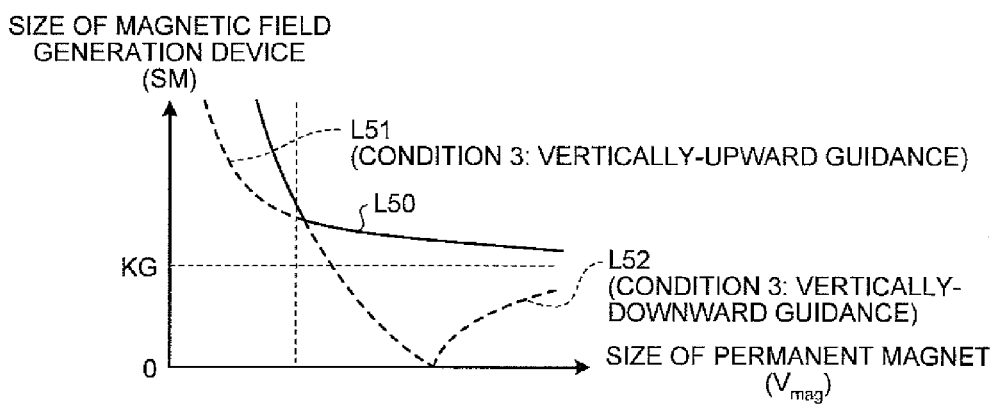
FIG. 16 is a graph representing the relationship between the size of a permanent magnet and the size of the magnetic field generation device under Condition 3 of Study 5.

Accordingly, the results represented in FIGS. 14 to 16 are obtained.

In other words, under Condition 1, the condition for minimizing the size SM of the magnetic field generation device 20 is the same as in the case of Study 4, where, $$Fdis2=2(Mcap-Vcap\times\rho liq)\times G \quad (22)$$

can be obtained from $$K\times|(V_{cap}\rho_{liq}-M_{cap})\times G+F_{dis2}|\div M_{mag}$$
$$=K\times|(M_{cap}-V_{cap}\times\rho_{liq})\times G|\div M_{mag}$$

Thus, the size SM of the magnetic field generation device 20 can be minimized by setting the size $V_{mag}$ of the permanent magnet 24 of the capsule body 2 such that the value obtained by doubling the difference between the gravitational force and buoyancy of the capsule body 2 is equal to the drag that the magnetic field generation device 20 generates on the capsule body 2 vertically upward. In other words, the minimum value can be obtained with respect to the composite curve of curve portions of the curve L30 of curved positions of the curve L31 and L32, where the size SM of the magnetic field generation device 20 is large. The optimum size of the permanent magnet 24 here is the size V4 indicated in FIG. 14 and is the value at the intersection of the curve L31 and the curve L32.

The maximum value of the force that the magnetic field generation device 20 generates vertically upward on the capsule body 2 is equal to the maximum value of the vertically downward force. The maximum values satisfy the following condition:

$$F_{down} = \tag{23}$$

$$F_{up} = |(M_{cap} - V_{cap} \times \rho_{liq}) \times G + F_{dis1}| < |(M_{cap} - V_{cap} \times \rho_{liq}) \times G + (V_{cap} \times \rho_{liq} - M_{cap-mag}) \times G| = M_{mag} \times G$$

Thus, the vertically upward or downward force is set to be smaller than the product of the mass of the permanent magnet 24 and the gravitational acceleration.

In contrast, under Condition 2, the size SM of the magnetic field generation device 20 is constant within the range of $SM_{up}$ (curve L41)$\geq SM_{down}$ (curve L42) (see curve L40). Thus, the size SM of the magnetic field generation device 20 can be reduced if $$F_{dis2} \leq 2(M_{cap} - V_{cap} \times \rho_{liq}) \times G \tag{24},$$

which is obtained from $$K \times |(V_{cap} \times \rho_{liq} - M_{cap}) \times G + F_{dis2}| \div M_{mag}$$

$$\leq K \times |(M_{cap} - V_{cap} \times \rho_{liq}) \times G| \div M_{mag}$$

Here, the maximum value of the vertically upward force that the magnetic field generation device 20 generates on the capsule body 2 increases to be more than the maximum value of the vertically downward force. The value can be represented by the following equation:

$$F_{up} = M_{mag} \times G \tag{25}$$

Thus, the vertically upward or downward force is set such that the product of the mass of the permanent magnet 24 and the gravitational acceleration is equal to the gravitational acceleration.

Under Condition 3, the condition for minimizing the size SM of the magnetic field generation device 20 is preferably that, as in the case of Condition 3 of Study 1, a permanent magnet as large as possible be arranged in the capsule body 2. The curve in this case is a composite curve L50 of curved portions of the curve L51 and the curve L52 in which the size SM is large, without extremes, and the size SM of the magnetic field generation device 20 decreases as the size $V_{mag}$ of the permanent magnet 24 increases.

It is desirable that a permanent magnet be arranged that is larger than the size $V_{mag}$ ($M_{mag}$) of the permanent magnet 24 with which the vertically upward force $F_{up}$ and the vertically downward force $F_{down}$ balance out (corresponding to the intersection of the curve L51 and the curve L52). With the curve L51, the size SM of the magnetic field generation device 20 decreases rapidly due to an increase in the size $V_{mag}$ ($M_{mag}$) of the permanent magnet 24. Thus, by increasing the size $V_{mag}$ ($M_{mag}$) of the permanent magnet 24 to be more than the intersection of the curve L51 and the curve L52, the effect of size reduction by increasing the size $V_{mag}$ ($M_{mag}$) of the permanent magnet can definitely be obtained (within the range of $SM_{up} \geq SM_{down}$). Accordingly, a setting is made for the permanent magnet 24, as in the case of Condition 2, such that it satisfies the following inequality:

$$F_{dis2} \leq 2(M_{cap} - V_{cap} \times \rho_{liq}) \times G \tag{26}$$

In this case, the maximum value of the vertically upward force that the magnetic field generation device 20 generates on the capsule body 2 is more than the maximum value of the vertically downward force. The maximum value satisfies the following inequality:

$$F_{up} \geq M_{mag} \times G \tag{27}$$

Thus, the vertically upward or downward force is set to be equal to or more than the product of the mass of the permanent magnet 24 and the gravitational acceleration.

As in the case of Study 1, the size $V_{mag}$ ($M_{mag}$) of the permanent magnet 24 may be set such that the absolute value of $SM_{down}$ be equal to or less than 0. In this case, because a vertically upward force is generated also for guiding the capsule body 2 vertically downward, it is unnecessary to generate a magnetic attraction vertically downward. Thus, an electromagnet for generating a magnetic attraction vertically downward is unnecessary, which further downsizes the magnetic field generation device 20. In this case, the size $V_{mag}$ ($M_{mag}$) of the permanent magnet 24 is set to satisfy the following condition:

(Absolute value of $SM_{down}$)

$$= -G + ((V_{cap} \times \rho_{liq} - M_{cap-mag}) \times G + F_{dis1} + F_{dis2})/M_{mag} \leq 0$$

$$((V_{cap} \times \rho_{liq} - M_{cap-mag}) \times G + F_{dis1} + F_{dis2}) \leq M_{mag} \times G$$

$$F_{dis1} + F_{dis2} \leq (M_{mag} + M_{cap-mag} - V_{cap} \times \rho_{liq}) \times G$$

$$F_{dis1} + F_{dis2} \leq (M_{cap} - V_{cap} \times \rho_{liq}) \times G$$

Here, $$F_{dis1} \leq (M_{cap} - V_{cap} \times \rho_{liq}) \times G \tag{28}$$

is obtained from $$F_{dis2} > 0$$

Accordingly, the force that is generated vertically upward satisfies the following equation:

$$F_{up} = |(M_{cap} - V_{cap} \times \rho_{liq}) \times G + F_{dis1}|$$

$$\leq (M_{cap} - V_{cap} \times \rho_{liq}) \times G + (M_{cap} - V_{cap} \times \rho_{liq}) \times G|$$

$$\leq 2 \times (M_{cap} - V_{cap} \times \rho_{liq}) \times G \tag{29}$$

Thus, it is desirable that the size of the permanent magnet 24 be set such that the force that the magnetic field generation device 20 generates on the capsule body 2 vertically upward be equal to or less than the value obtained by multiplying, by the gravitational acceleration, the value obtained by doubling the difference between the mass of the capsule body 2 and the product of the volume of the capsule body 2 and the density of the liquid 40 (the buoyancy acting on the capsule body 2).

System Application Example: Capsule Medical Apparatus Guidance System

Figure 17:
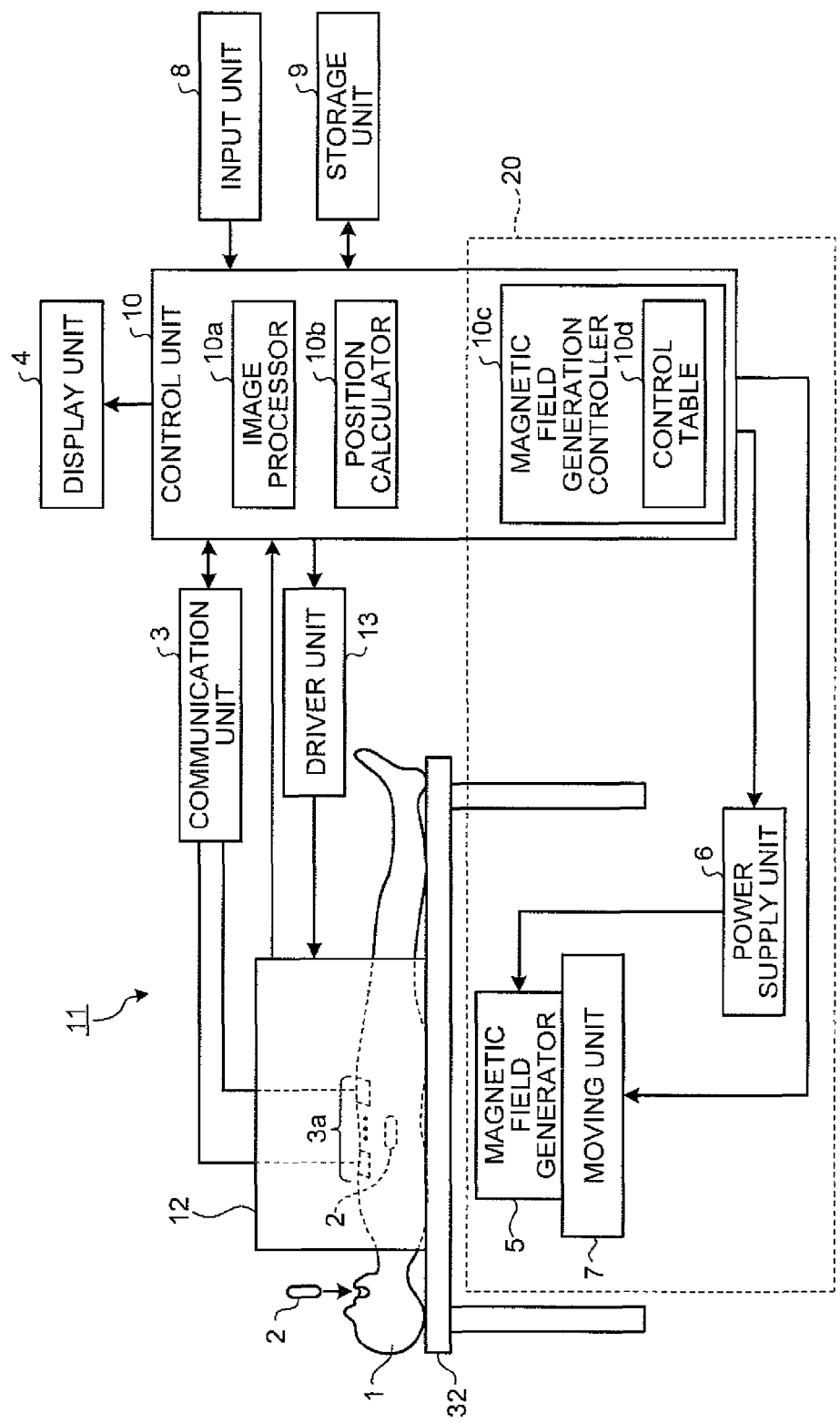
FIG. 17 is a schematic diagram of a configuration of a capsule medical apparatus guidance system according to an embodiment of the present invention.

FIG. 17 is a schematic diagram of a configuration of a capsule medical apparatus guidance system that guides the capsule body that is optimized for examinations. A capsule medical apparatus guidance system 11 inserts a capsule medical apparatus (capsule body) 2 into a subject 1 and in-vivo images captured or samples of in-vivo of tissues are taken while the capsule body 2 is guided in the subject 1. The system includes a communication unit 3 that communicates by radio with the capsule body 2 in the subject 1 via multiple antennae 3a that are arranged on the body surface of the subject 1; a display unit 4 that displays various types of information, such as in-vivo images of the subject 1, which are captured by the capsule body 2; a magnetic field generator 5 that generates a magnetic field for guiding the capsule body 2 in the subject 1; a power supply unit 6 that supplies power to the magnetic field generator 5; a moving unit 7 that moves the magnetic field generator 5; an input unit 8 that inputs various types of information, such as the type of the capsule body 2 that is inserted; a storage unit 9 that stores various types of information, such as in-vivo images of the subject 1; a position detecting device 12 that detects the position of the capsule body 2 in the subject 1; a drive unit 13 that drives magnetic fields that are used by the position detecting device 12; and a control unit 10 that controls the above-described components.

The magnetic field generator 5 is realized by using multiple electromagnets. The magnetic field generator 5 generates a three-dimensional external magnetic field, such as a rotation magnetic field or a gradient magnetic field, by using power that is supplied from the power supply unit 6. Specifically, the magnetic field generator 5 can generate at least a magnetic field that has a gradient with respect to the vertical direction. The magnetic field generator 5 applies an external magnetic field to the capsule body 2 in the subject 1, who is lying on a bed 32, and generates a magnetic attraction with the permanent magnet 24 in the subject 1 using the effects of the external magnetic field, thereby guiding the capsule body 2 to a desired in-vivo site.

The moving unit 7 moves the magnetic field generator 5 relative to the subject 1 such that the external magnetic field, which is generated by the magnetic field generator 5, is applied to the capsule body 2 in the subject 1. Specifically, an X-Y plane is set that is approximately parallel to the surface of the bed 32 on which the subject 1 lays. The moving unit 7 moves the magnetic field generator 5 to a coordinate position on the X-Y plane under the control of the control unit 10. In this case, the moving unit 7 moves the magnetic field generator 5 such that the capsule body 2 in the subject 1 is positioned in the three-dimensional space in which the external magnetic field is generated by the magnetic field generator 5.

The input unit 8 may be realized using input devices, such as a keyboard, a mouse, and a joystick. In response to an input operation by a user, such as a doctor or a nurse, the input unit 8 inputs various types of information to the control unit 10. The input unit 8 also functions as an operation means that manipulates control by the control unit 10 on the basis of the result displayed by the display unit 4. Various types of information that the input unit 8 inputs to the control unit 10 include, for example, instruction information for instructions to the control unit 10, patient information on the subject, and examination information on the subject. Particularly, information on the type (size or density) of the capsule body 2 is input.

The control unit 10 includes an image processor 10a that generates in-vivo images of the subject 1, a position calculator 10b that calculates the position of the capsule body 2 in the subject 1, and a magnetic field generation control unit 10c that controls the intensity of the magnetic field, which is generated by the magnetic field generator 5, by controlling the amount of power supplied from the power supply unit 6 to the magnetic field generator 5.

The image processor 10a acquires the image signals, which are obtained by demodulating the radio signals from the capsule body 2, from the communication unit 3, performs predetermined image processing on the acquired image signals, and generates image information corresponding to the image signals, i.e., in-vivo images of the subject 1. A group of in-vivo images, which are generated by the image processor 10a, is displayed on the display unit 4 and stored in the storage unit 9.

The position calculator 10b detects the position of the capsule body 2 on the basis of a signal that is output by the position detecting device 12 that detects a detection magnetic field, which is generated from an LC marker in the capsule body 2 according to the magnetic field generated by the drive unit 13. The result of the position detection is displayed on the display unit 4 and is stored in the storage unit 9. The operator inputs, via the input unit 8, guidance instruction information for guiding the capsule body 2 on the basis of the position of the capsule body 2, which is displayed on the display unit 4, in order to perform guidance control.

The magnetic field generation control unit 10c controls the guidance of the capsule body 2 by controlling the intensity of the magnetic field, which is generated by the magnetic field generator 5, on the basis of the input guidance instruction information. The magnetic field generation control unit 10c includes a control table 10d. The control table 10d is a table in which the optimum maximum magnetic field that can be generated, information on the types of the capsule body 2 that is input from the input unit 8, and examination information (examination contents) are associated. The magnetic field generation control unit 10c performs magnetic field generation control, in which the optimum maximum magnetic field that can be generated is limited, with reference to the control table 10d and according to the information on the types of the capsule body 2 and the examination information.

Regarding the capsule body 2, there is a premise that the size $V_{mag}$ of the external permanent magnet 24 is optimized in accordance with the above-described studies. In addition, the magnetic filed generation control unit 10c performs power transmission control for generating a magnetic field necessary for guidance in the range of the optimum maximum magnetic field that can be generated, as described above, according to the information on the type of the capsule body 2 inserted into the subject 1 and the examination information. Accordingly, power can be saved in accordance with each type of the capsule body 2 and the examination contents. In a system in which the type of the capsule body 2 used by the capsule medical apparatus guidance system 11 and the examination contents are specified, the size SM of the magnetic field generation device 20 can be minimized, which further reduces the size.

The contents of the control table 10d will be described using specific examples. Here, the maximum magnetic field is set according to the capsule type and examination contents. For example, the following correspondence relations C-1 to C-5 are described.

C-1) Capsule Type: Density is Approximately 1 g/cm$^3$, Size (Small)

Examination contents: Observation of the esophagus (cardiac end) and the stomach (passing through the pylorus by peristalsis)

Maximum magnetic field (Size of magnetic field generation device): Small

C-2) Capsule Type: Density is More than 1 g/cm$^3$, Size (Small)

Examination contents: Observation of the esophagus (cardiac end), the stomach, and the duodenum (passing through the pylorus by guidance)

Maximum magnetic field (Size of magnetic field generation device): Medium

C-3) Capsule Type: Density is More than 1 g/cm³, Size (Small)
  Examination contents: Observation of all digestive canals (Guidance)
  Maximum magnetic field (Size of magnetic field generation device): Large
C-4) Capsule Type: Size (Large)
  Examination contents: Not specified
  Maximum magnetic field (Size of magnetic field generation device): Small
C-5) Capsule Type: Size (Large)
  Examination contents: Examination of the large intestine
  Maximum magnetic field (Size of magnetic field generation device): Large The size of the magnetic field generation device 20 in this case is determined according to C-3 or C-5, which requires the maximum magnetic field. As described in the studies, the maximum magnetic field may be set in more detail according to the guidance direction or a combination of guidance directions. Alternatively, the size SM of the magnetic field generation device 20 may be determined in more detail according to the guidance direction or a combination of guidance directions.

The descriptions are provided above on the premise that the system guides the capsule body 2 by generating a magnetic attraction with the permanent magnet 24 in the capsule body 2 by using the generation of a magnetic gradient. However, for example, the capsule body 2 may be guided in a way that the capsule body 2 is provided with a spiral structure on its outer surface and is arranged such that the magnetization direction of the permanent magnet is vertical to the center axis of the spiral, and thus the magnetic field generation device 20 generates a rotational magnetic field. In this case, even if the canal in the small intestine and the canal in the large intestine are not sufficiently expanded and the pressure from the intestinal walls is large, the contact with the intestinal walls can be utilized to guide the capsule body more efficiently by the rotation spiral method, which leads to further size reduction of the magnetic field generation device 20.

According to the embodiments described above, a mass of a capsule body excluding a permanent magnet is less than a product of a volume of the capsule body and a density of a liquid, and a magnetic field generation device guides the capsule body while a maximum value of a magnetic attraction that the magnetic field generation device generates vertically upward on the capsule body is equal to a maximum value of a magnetic attraction that the magnetic field generation device generates vertically downward on the capsule body and the maximum value of the magnetic attraction that is generated vertically upward or downward is less than a value that is obtained by multiplying a mass of the permanent magnet by a gravitational acceleration. Thus, the magnetic field generation device can be downsized.

According to the embodiments described above, a mass of a capsule body excluding a permanent magnet is less than a product of a volume of the capsule body and a density of a liquid, and the magnetic field generation device guides the capsule body while a maximum value of a magnetic attraction that the magnetic field generation device generates vertically upward on the capsule body is equal to or more than a maximum value of a magnetic attraction that the magnetic field generation device generates vertically downward on the capsule body and the maximum value of the magnetic attraction that is generated vertically upward or downward is equal to or more than a value that is obtained by multiplying a mass of the permanent magnet by a gravitational acceleration. Thus, the magnetic field generation device can be downsized.

According to the embodiments described above, a mass of a capsule body excluding a permanent magnet is less than a product of a volume of the capsule body and a density of a liquid, the capsule body includes a plurality of capsule main bodies that are in multiple types and different in any one of size of the permanent magnet, volume of the capsule body, or shape of the capsule body, and the magnetic field generation device changes a maximum magnetic attraction that is generated on the capsule body in accordance with the type of the capsule body that is input by an input unit. Thus, the magnetic field generation device can be downsized and the power can be saved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical apparatus guidance system, comprising:
  a plurality of capsule bodies including a first capsule body and a second capsule body;
  the first capsule body includes a first casing which can be introduced into a subject in order to perform, in a liquid, examination of or treatment on the interior of the subject, the first casing containing a first permanent magnet, a mass of the casing excluding the first permanent magnet being set to be less than a product of a volume of the first casing and a density of the liquid;
  the second capsule body includes a second casing which can be introduced into the subject in order to perform, in the liquid, examination of or treatment on the interior of the subject, the second casing containing a second permanent magnet, a mass of the second casing excluding the second permanent magnet being set to be less than a product of a volume of the second casing and the density of the liquid;
  a magnetic field generation device comprising a magnetic field generator and a magnetic field generation control unit;
  the magnetic field generator generates a magnetic field for the first and second permanent magnets to generate a magnetic attraction vertically upwards and vertically downwards to guide the first and second capsule bodies;
  the magnetic field generation control unit controls the magnetic field generator to generate the magnetic field by setting a maximum value of the magnetic attraction that is generated vertically upward to the first capsule body and the second capsule body and a maximum value of the magnetic attraction that is generated vertically downward to the first capsule body and the second capsule body;
  an input unit configured to input information on capsule body types including one or more of size and density of the plurality of capsule bodies that is guided by the magnetic attraction that is generated by the magnetic field generator; and
  the magnetic field generation control unit causes the magnetic field generator to change the maximum value of the magnetic attraction generated vertically upwards to the first capsule body and the second capsule body such that the magnetic field generation control unit sets the maximum value of magnetic attraction that is generated vertically upward with respect to the first capsule body and the second capsule body corresponding to the information on capsule body types input by the input unit, the maximum value of magnetic attraction that is generated vertically upwards for the first capsule body and the second capsule body is equal to or less than a value that is obtained by doubling a difference between a mass of the plurality of capsule bodies and a product of a volume of the plurality of capsule bodies and the density of the liquid and then multiplying the doubled difference by a gravitational acceleration.

* * * * *